(12) United States Patent
Van Egmond

(10) Patent No.: US 7,151,198 B2
(45) Date of Patent: Dec. 19, 2006

(54) INTEGRATION OF A METHANOL SYNTHESIS SYSTEM WITH A METHANOL TO OLEFIN REACTION SYSTEM

(75) Inventor: Cor F. Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 487 days.

(21) Appl. No.: 10/403,271

(22) Filed: Mar. 28, 2003

(65) Prior Publication Data

US 2004/0127759 A1 Jul. 1, 2004

Related U.S. Application Data

(60) Provisional application No. 60/436,925, filed on Dec. 30, 2002.

(51) Int. Cl.
  C07C 1/02 (2006.01)
  C07C 1/04 (2006.01)
  C07C 1/06 (2006.01)

(52) U.S. Cl. ...................... 585/327; 585/324

(58) Field of Classification Search ............... 585/327, 585/324
  See application file for complete search history.

(56) References Cited

U.S. PATENT DOCUMENTS

| | | | |
|---|---|---|---|
| 4,497,968 A | 2/1985 | Wright et al. | 585/304 |
| 4,827,046 A | 5/1989 | Harandi et al. | 568/697 |
| 4,831,195 A | 5/1989 | Harandi et al. | 568/697 |
| 4,849,575 A * | 7/1989 | Lewis | 585/640 |
| 4,886,651 A | 12/1989 | Patel et al. | 423/359 |
| 4,981,491 A | 1/1991 | Harandi et al. | 44/448 |
| 5,009,859 A | 4/1991 | Harandi et al. | 422/189 |
| 5,026,529 A | 6/1991 | Harandi et al. | 422/190 |
| 5,026,934 A | 6/1991 | Bains et al. | 585/314 |
| 5,028,400 A | 7/1991 | Harandi et al. | 422/211 |
| 5,047,070 A | 9/1991 | Harandi et al. | 44/446 |
| 5,064,623 A | 11/1991 | Harandi et al. | 422/190 |
| 5,130,101 A | 7/1992 | Harandi et al. | 422/189 |
| 5,346,593 A | 9/1994 | Cialkowski et al. | 203/18 |
| 5,430,219 A | 7/1995 | Sanfilippo et al. | 585/659 |
| 5,512,599 A | 4/1996 | Hiramatsu et al. | 518/703 |
| 5,599,955 A | 2/1997 | Vora et al. | 549/525 |
| 5,714,662 A | 2/1998 | Vora et al. | 585/640 |
| 6,100,303 A | 8/2000 | Hirotani et al. | 518/703 |
| 6,114,400 A | 9/2000 | Nataraj et al. | 518/715 |
| 6,444,712 B1 | 9/2002 | Janda | 518/706 |
| 6,495,609 B1 | 12/2002 | Searle | 518/700 |

OTHER PUBLICATIONS

U.S. Appl. No. 10/124,859, filed Apr. 18, 2002, Van Egmond et al.
U.S. Appl. No. 10/125,138, filed Apr. 18, 2002, Van Egmond et al.

* cited by examiner

*Primary Examiner*—Thuan Dinh Dang

(57) ABSTRACT

Disclosed is a process for producing light olefins in an integrated methanol synthesis/MTO reaction system. The integrated system implements a shared separation system for separating oxygenate components from the respective methanol synthesis system and MTO reaction system. By providing a shared separation system, the number of separation units in an integrated methanol/MTO reaction system may be advantageously reduced.

15 Claims, 4 Drawing Sheets

US 7,151,198 B2

INTEGRATION OF A METHANOL SYNTHESIS SYSTEM WITH A METHANOL TO OLEFIN REACTION SYSTEM

This application claims benefit of 60/436,925 filed Dec. 30, 2002.

FIELD OF THE INVENTION

The present invention relates to integrating a methanol synthesis system with a methanol-to-olefin reaction system and particularly to implementing a shared distillation system for processing crude methanol from the methanol synthesis system and byproducts from the methanol-to-olefin reaction system.

BACKGROUND OF THE INVENTION

Olefins have been traditionally produced from petroleum feedstock by catalytic or steam cracking processes. These cracking processes, especially steam cracking, produce light olefins such as ethylene and propylene from a variety of hydrocarbon feedstock. Ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefins. For example, methanol, the preferred alcohol for light olefin production, may be converted to primarily ethylene and propylene in the presence of a molecular sieve catalyst. This process is referred to as a methanol-to-olefin (MTO) reaction process, which occurs in an MTO reaction system.

There are numerous technologies available for producing methanol including fermentation or the reaction of synthesis gas (syngas) derived from a hydrocarbon feed stream, which may include natural gas, petroleum liquids, carbonaceous materials including coal, recycled plastics, municipal waste or any other organic material. Methanol is typically synthesized from the catalytic reaction of syngas in a methanol reactor in the presence of a heterogeneous catalyst. For example, in one synthesis process methanol is produced using a copper/zinc oxide catalyst in a water-cooled tubular methanol reactor. Syngas is defined as a gas comprising primarily carbon monoxide (CO), hydrogen ($H_2$) and preferably carbon dioxide ($CO_2$). Optionally, syngas may also include unreacted feedstocks such as methane ($CH_4$), ethane, propane or heavier hydrocarbons. Generally, the production of syngas involves a reforming reaction of natural gas, mostly methane, and an oxygen source into hydrogen, carbon monoxide and/or carbon dioxide. Syngas production processes are well known, and include conventional steam reforming, autothermal reforming, or a combination thereof.

In an effort to increase energy and capital cost savings as well as olefin yield, U.S. Pat. No. 5,714,662 to Vora et al., the entirety of which is incorporated herein by reference, discloses integrating a methanol synthesis system with an MTO reaction system. Specifically, the Vora patent discloses a process for the production of light olefins from a hydrocarbon gas stream by a combination of reforming, oxygenate production, and oxygenate conversion wherein a crude methanol stream—produced in the production of oxygenates and comprising methanol, light ends, and heavier alcohols—is passed directly to the oxygenate conversion zone for the production of light olefins. The fusel oil in the crude methanol, which typically includes higher alcohols and is generally burned as a fuel in the methanol plant, is passed to the oxygenate conversion process for the additional production of light olefins. The Vora patent indicates that in so doing, the yield of ethylene, propylene, and butylenes can be enhanced at significant capital and operating cost savings by not requiring a complex and expensive distillation train for the production of high purity methanol.

A typical MTO reaction system may include an oxygenate/MTO byproduct separation system, which is adapted to separate unreacted oxygenates from MTO byproducts such as water. A typical methanol synthesis system includes a light ends separation system for separating light ends, e.g., unreacted syngas components, and product methanol from water, caustic salts, and fusel oil, e.g., C1–C4 alcohols and water, which are byproducts of the methanol synthesis process. Each of these separation systems may include one or more expensive and space-consuming separation units, e.g., distillation columns, pumps and heat exchangers. Thus, the need exists for reducing the number of these separation units.

SUMMARY OF THE INVENTION

This invention provides an integrated methanol synthesis and methanol-to-olefin (MTO) reaction system. Specifically, the integrated system implements a shared separation system for processing crude methanol from the methanol synthesis system and byproducts from the methanol-to-olefin reaction system. By providing a shared separation system, the number of separation units in an integrated methanol/MTO reaction system may be advantageously reduced, and a commensurate decrease in capital cost and operating costs can be realized.

In one embodiment, the invention provides a process for producing light olefins. The process includes providing a syngas stream comprising syngas, wherein the syngas comprises hydrogen, carbon monoxide and carbon dioxide. At least a portion of the syngas in the syngas stream is converted to methanol and water in a methanol-containing stream. Water is removed from at least a portion of the methanol-containing stream in a separation unit to form a dry methanol stream containing methanol. At least a portion of the dry methanol stream is directed to an MTO reactor, in which the methanol in the at least a portion of the dry methanol stream contacts a molecular sieve catalyst in the MTO reactor under conditions effective to form an effluent stream comprising the light olefins and water. At least a portion of the effluent stream is directed to the separation unit, and water is removed from the at least a portion of the effluent stream in the separation unit.

In another embodiment, the invention includes providing a syngas stream comprising syngas, wherein the syngas comprises hydrogen, carbon monoxide and carbon dioxide. At least a portion of the syngas in the syngas stream is converted to methanol and water in a methanol-containing stream. At least a portion of the methanol-containing stream in a light ends removal unit is separated into a first fraction and a second fraction, wherein the first fraction contains light ends including hydrogen, carbon monoxide and carbon dioxide, and wherein the second fraction contains a majority of the methanol and water from the methanol-containing stream. Water is removed from at least a portion of the second fraction in a first separation unit to form a dry methanol stream and a water-containing stream, wherein the dry methanol stream comprises methanol from the second fraction, and wherein the water-containing stream comprises water from the second fraction. At least a portion of the dry methanol stream is directed to an MTO reactor, wherein the methanol in the dry methanol stream contacts a molecular sieve catalyst in the MTO reactor under conditions effective to form an effluent stream comprising the light olefins and water. At least a portion of the effluent stream is separated into a third fraction and a fourth fraction, wherein the third fraction contains a majority of the C2–C5 olefins present in the at least a portion of the effluent stream, and wherein the fourth fraction contains a majority of the water and methanol present in the at least a portion of the effluent stream. Water is removed from at least a portion of the fourth fraction in the first separation unit, wherein the dry methanol stream further comprises methanol from the at least a portion of the fourth fraction, and wherein the water-containing stream further comprises water from the at least a portion of the fourth fraction.

The present invention also provides a process for producing light olefins, which process includes converting syngas in a methanol synthesis unit into methanol and water in a methanol-containing stream. Water is removed from the methanol-containing stream in a distillation column, and methanol from the distillation column contacts a catalyst in an MTO reactor under conditions effective to form a first effluent stream containing water and the light olefins. The process also includes separating a majority of the light olefins from the first effluent stream to form a light olefins stream and a second effluent stream, wherein the second effluent stream contains a majority of the water from the first effluent stream and less than 10 weight percent light olefins, based on the total weight of the second effluent stream. Water is removed from at least a portion of the second effluent stream in the distillation column.

In another embodiment of the present invention, a syngas stream in a methanol synthesis reactor is converted to a first effluent stream containing methanol and water. The first effluent stream is separated in a separation unit into a first fraction and a second fraction, wherein the first fraction comprises a majority of the methanol present in the first effluent stream, and wherein the second fraction comprises a majority of the water present in the first effluent stream. The process also includes contacting the methanol in the first fraction with a catalyst in an MTO reactor under conditions effective to form a product effluent containing the light olefins, residual methanol and water. The product effluent is separated into one or more C2–C5 product streams, and a third fraction, wherein the third fraction contains a majority of the residual methanol and water present in the product effluent. In the separation unit, a majority of the residual methanol present in the third fraction is separated from a majority of the water present in the third fraction, wherein the first fraction further comprises the majority of the residual methanol present in the third fraction, and wherein the second fraction further comprises the majority of the water present in the third fraction.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

A. Introduction

Figure 1:
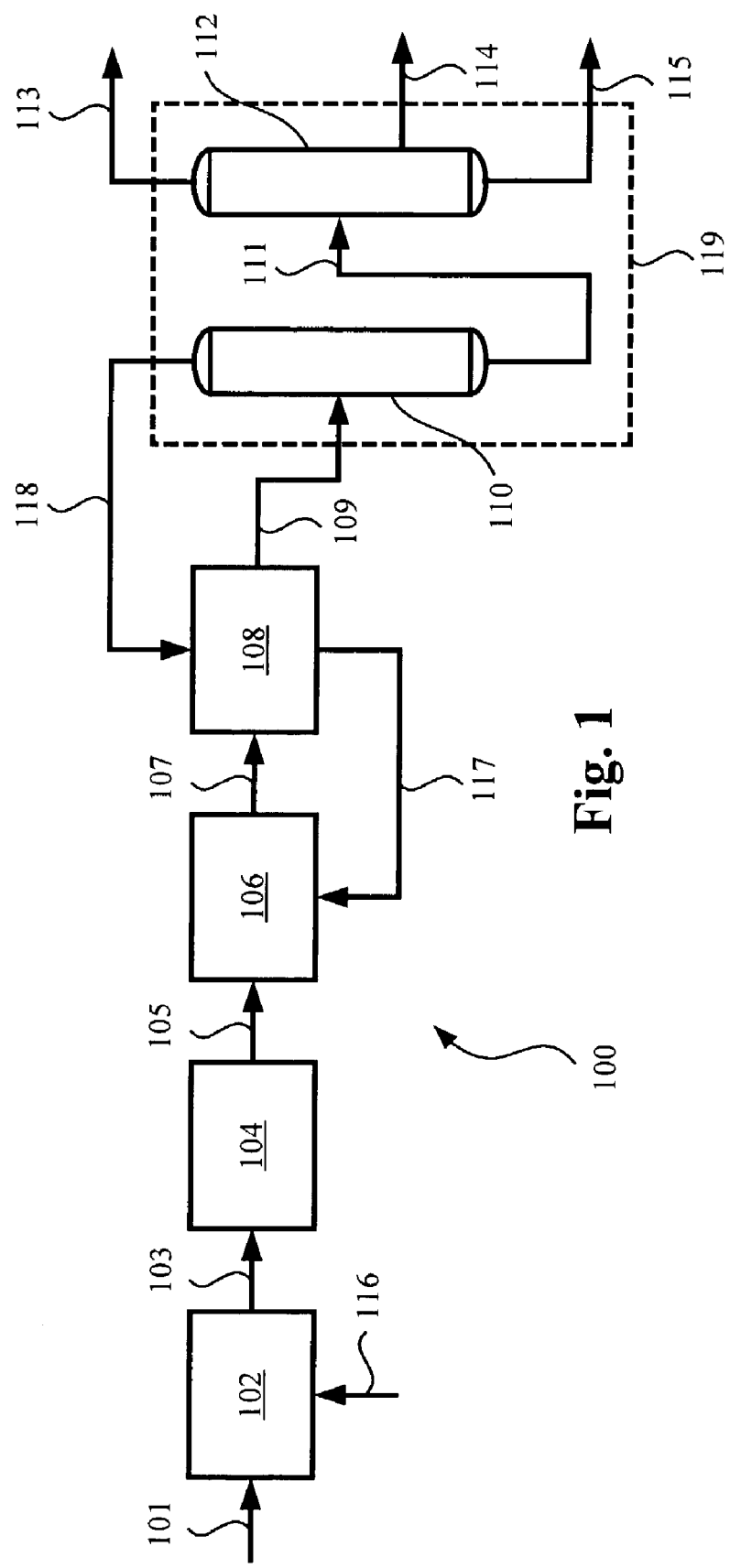
FIG. 1 is a flow diagram of a methanol synthesis system.

The present invention provides an integrated methanol synthesis and MTO reaction system including a shared methanol/water separation system. The shared methanol/water separation system receives a crude methanol stream from the methanol synthesis system and byproducts from the MTO reaction system. The methanol/water separation system separates methanol from these streams in a single distillation system for recycle back to the feed vaporization and introduction system and the MTO reactor unit. By providing a shared separation system, the number of separation units in an integrated methanol/MTO reaction system may be advantageously reduced, and a commensurate decrease in capital cost and operating costs can be realized.

B. Methanol Synthesis Systems
1. Examples of Methanol Synthesis Processes

Methanol compositions can be manufactured from a hydrocarbon feed stream derived from a variety of carbon sources. Examples of such sources include biomass, natural gas, C1–C5 hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

One way of converting the carbon source to a methanol composition is to first convert the carbon source to synthesis gas (syngas), and then convert the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

Syngas is defined as a gas comprising primarily carbon monoxide (CO), carbon dioxide ($CO_2$) and hydrogen ($H_2$). Optionally, syngas may also include methane ($CH_4$), and small amounts of ethane and propane. Conventional processes for converting carbon components to syngas include steam reforming, partial oxidation, autothermal reforming, and combinations of these processes.

The hydrocarbon feed stream that is used in the conversion of hydrocarbon to synthesis gas is optionally treated to remove impurities that can cause problems in further processing of the hydrocarbon feed stream. These impurities can poison many conventional propylene and ethylene forming catalysts. A majority of the impurities, which may be present, can be removed in any conventional manner. The hydrocarbon feed is preferably purified to remove sulfur compounds, nitrogen compounds, particulate matter, other condensables, and/or other potential catalyst poisons prior to being converted into synthesis gas.

In one embodiment of the invention, the hydrocarbon feed stream is passed to a synthesis gas plant. Synthesis gas refers to a combination of hydrogen and carbon oxides produced in a synthesis gas plant from a hydrocarbon feed, the synthesis gas having an appropriate molar ratio of hydrogen to carbon oxides (carbon monoxide and carbon dioxide), as described below. The synthesis gas plant may employ any conventional means of producing synthesis gas, including partial oxidation, steam or $CO_2$ reforming, or some combination of these chemistries. Steam reforming generally comprises contacting a hydrocarbon with steam to form synthesis gas. The process preferably includes the use of a catalyst.

Partial oxidation generally comprises contacting a hydrocarbon with oxygen or an oxygen containing gas such as air to form synthesis gas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional synthesis gas-generating processes include gas phase partial oxidation, autothermal reforming, fluid bed synthesis gas generation, catalytic partial oxidation and various processes for steam reforming.

2. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \leftrightarrows CO + 3H_2 \qquad (1)$$

or $$C_nH_m + nH_2O \leftrightarrows nCO + [n+(m/2)]H_2 \qquad (2)$$

and $$CO + H_2O \leftrightarrows CO_2 + H_2 \qquad (3) \text{ (shift reaction)}$$

The reaction is carried out in the presence of a catalyst. Any conventional reforming type catalyst can be used. The catalyst used in the step of catalytic steam reforming comprises at least one active metal or metal oxide of Group 6 or Group 8–10 of the Periodic Table of the Elements. The Periodic Table of the Elements referred to herein is that from CRC Handbook of Chemistry and Physics, 82nd Edition, 2001–2002, CRC Press LLC, which is incorporated herein by reference.

In one embodiment, the catalyst contains at least one Group 6 or Group 8–10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8–10 metals in the catalyst can vary. Preferably, the catalyst includes from about 3 wt % to about 40 wt % of at least one Group 6 or Group 8–10 metal, based on total weight of the catalyst. Preferably, the catalyst includes from about 5 wt % to about 25 wt % of at least one Group 6 or Group 8–10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Weight hourly space velocity in the reformer should be sufficient for providing the desired CO to $CO_2$ balance in the synthesis gas. Weight hourly space velocity in Syngas generation is the total weight of the feedstock fed to the reaction zone per hour per weight of catalyst composition in the reaction zone. Preferably, the weight hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, Encyclopedia of Chemical Technology, 3rd Ed., 1990, vol. 12, p. 951; and Ullmann's Encyclopedia of Industrial Chemistry, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ratio of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

3. Partial Oxidation to Make Syngas

The invention further provides for the production of synthesis gas, or CO and $H_2$, by oxidative conversion (also referred to herein as partial oxidation) of a hydrocarbon, particularly natural gas and $C_1$–$C_5$ hydrocarbons. According to the process, the hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightarrows nCO + (m/2)H_2 \quad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminium titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) molar ratio of from about 1.2:1 to about 10:1. Preferably the feed and oxygen are injected into the reformer at a methane to oxygen molar ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane molar ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about 103 cm3/g·hr to about 105 cm3/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \leftrightharpoons H_2+CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon molar ratio in the range of from about 0.3:1 to about 0.8:1, more preferably, in the range of from about 0.45:1 to about 0.75:1. References herein to the oxygen-to-carbon molar ratio refer to the ratio of oxygen in the form of oxygen molecules ($O_2$) to carbon atoms present in the hydrocarbon feedstock. Preferably, the oxygen-to-carbon molar ratio is in the range of from about 0.45:1 to about 0.65:1, with oxygen-to-carbon ratios in the region of the stoichiometric ratio of 0.5:1, that is molar ratios in the range of from about 0.45:1 to about 0.65:1, being more preferred.

When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

4. Autothermal Reforming to Make Syngas

Autothermal reforming processes can also be incorporated into this invention. Autothermal reforming involves a combination of gas phase partial oxidation and steam reforming chemistry.

In one autothermal reforming process, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with oxygen or an oxygen-containing gas, e.g., air, and residual hydrocarbons, and the mixed gas is partially oxidized to carbon monoxides.

In another embodiment, the autothermal reforming process comprises a primary oxidation process and a secondary steam reforming process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion. Alternatively, the two process are conducted in separate reactor units.

Preferably, the autothermal reforming is conducted as a fixed bed syngas generation process. In the fixed bed syngas generation process, hydrocarbon feed and oxygen or an oxygen-containing gas are introduced separately into a fixed catalyst bed.

The fixed bed syngas generation process is a combined process wherein methane is reacted with oxygen and steam. The fixed bed syngase generation process preferably is carried out at conditions of elevated temperatures and pressures that favor the formation of hydrogen and carbon monoxide. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

5. Converting Syngas to Methanol

The synthesis gas is sent to a methanol synthesis process and converted to a methanol composition. The methanol synthesis gas process is accomplished in the presence of a methanol synthesis catalyst.

In one embodiment, the synthesis gas is sent as is to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides ($CO+CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas.

Desirably, the stoichiometric molar ratio is sufficiently high so as maintain a high yield of methanol, but not so high as to reduce the volume productivity of methanol. Preferably, the synthesis gas fed to the methanol synthesis has a stoichiometric molar ratio (i.e., a molar ratio of $H_2$:($2CO+3CO_2$)) of from about 1.0:1 to about 2.7:1, more preferably from about 1.1 to about 2.0, more preferably a stoichiometric molar ratio of from about 1.2:1 to about 1.8:1.

The $CO_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a molar ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the molar ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

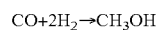

$CO+2H_2 \rightarrow CH_3OH$

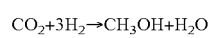

$CO_2+3H_2 \rightarrow CH_3OH+H_2O$

The methanol synthesis process is effective over a wide range of temperatures. In one embodiment, the synthesis gas is contacted with the methanol synthesis catalyst at a temperature in the range of from about 302° F. (150° C.) to about 842° F. (450° C.), preferably in a range of from about 347°

F. (175° C.) to about 662° F. (350° C.), more preferably in a range of from about 392° F. (200° C.) to about 572° F. (300° C.).

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Weight hourly space velocities in methanol synthesis vary depending upon the type of continuous process that is used. Desirably, the weight hourly space velocity of flow of gas through the catalyst bed is in the range of from about 50 hr-1 to about 50,000 hr-1. Preferably, the weight hourly space velocity of flow of gas through the catalyst bed is in the range of from about 250 hr-1 to about 25,000 hr-1, more preferably from about 500 hr-1 to about 10,000 hr-1.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

6. Refining Crude Methanol to Make Methanol Product

In conventional methanol synthesis systems, the crude methanol product mixture is further processed after reaction to obtain the methanol composition. Processing is accomplished by any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol and desirable aldehydes and/or other desirable alcohols also present.

In one processing system, the crude methanol product from the methanol synthesis reactor is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another processing system, the crude methanol is sent from the methanol synthesizing unit to a distillation system. The distillation system contains one or more distillation columns which are used to separate the desired methanol composition from water and hydrocarbon by-product streams. Desirably, the methanol composition that is separated from the crude methanol comprises a majority of the methanol and a majority of aldehyde and/or alcohol supplements contained in the crude alcohol prior to separation. Preferably, the methanol composition that is separated from the crude methanol comprises a majority of the acetaldehyde and/or ethanol contained in the crude methanol prior to separation. More preferably, the methanol composition that is separated from the crude methanol is one of the preferred methanol compositions of this invention.

The distillation system optionally includes a step of treating the methanol stream being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH is added.

The invention can include any distillation system that produces a "fusel oil" stream, which includes C1–C4 alcohols and water. The fusel oil stream has a boiling point higher than that of methanol. It is especially advantageous when the fusel oil stream is liquid taken from a column fed with the crude methanol from the let-down vessel or with the bottoms liquid from a column fed with such crude methanol, the off-take point being at a level below the feed level. Alternatively or additionally, the fusel oil stream is taken from a level above the feed level in such a column. Because some of the higher alcohols are advantageous in the methanol composition of this invention, it is desirable to operate the distillation system to recover the $C_2$–$C_4$ alcohols along with the methanol rather than in the fusel oil stream.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "refining column" from which methanol product is taken as an overhead stream or at a high level, and water is removed as a bottoms stream. In this embodiment, the refining column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or refining column. The semi-crude methanol is passed to a refining column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

A methanol synthesis system, generally designated by numeral 100, is illustrated in FIG. 1 and will now be described in greater detail. As shown in FIG. 1, a feed stream 101, which preferably includes natural gas, is directed to a desulfurization unit 102. Prior to entering the desulfurization unit 102, the feed stream 101 optionally is compressed by one or more compressors, not shown, to facilitate movement of the feed stream 101 and various intermediate streams through the methanol synthesis system 100. In one embodiment, the natural gas from feed stream 101 contacts water from water stream 116 in the desulfurization unit 102 in a countercurrent manner under conditions effective to remove sulfur-containing components, e.g., $H_2S$ and/or mercaptans, therefrom. In this manner, the desulfurization unit 102 acts as an absorption unit. Additionally or alternatively, the desulfurization unit 102 may act as an adsorption unit. In this embodiment, the desulfurization unit 102 preferably includes one or more columns that are packed with molecular sieve particles, e.g., 3–5 angstrom molecular sieve particles, the pores of which are adapted to capture the sulfur-containing components from feed stream 101. The adsorption unit optionally includes a regeneration system, not shown, for regenerating deactivated or partially deactivated molecular sieve particles. If the desulfurization unit 102 includes an adsorption unit, the feed stream 101 preferably is heated to a temperature of from 700° F. (371° C.) to 800° F. (427° C.) by a heat exchanger, not shown, before it is directed to desulfurization unit 102. The desulfurization unit 102 forms desulfurized feed stream 103, which is directed to a reforming unit 104. Preferably, desulfurized feed stream 103 comprises less than 5 weight percent, more preferably less than 1 weight percent, and most preferably less than 0.01 weight percent sulfur and sulfur-containing compounds, based on the total weight of the desulfurized feed stream 103.

The reforming unit 104 converts the natural gas in desulfurized feed stream 103 to syngas in syngas stream 105. The production of syngas, as discussed above, optionally involves a combustion reaction of natural gas, mostly methane, and an oxygen source, e.g., air, into hydrogen, carbon monoxide and/or carbon dioxide. Other syngas production processes are well known, and include conventional steam reforming, autothermal reforming, or a combination thereof. Thus, reforming unit 104 may be a steam reforming unit, a partial oxidation unit, an autothermal reforming unit, and/or a combined reforming unit, e.g., a unit that combines two or more of these reforming processes. In one embodiment, water from water stream 116 preferably increases the water content of, and more preferably saturates, the feed stream 101, in the process of removing sulfur-containing components. Additionally or alternatively, the desulfurized feed stream 103 is directed to a separate saturization unit, not shown, in which water contacts the desulfurized feed stream 103 under conditions effective to saturate the desulfurized feed stream 103 or increase the water content thereof. For example, the saturization unit may include a packed or tray column wherein water contacts the desulfurized feed stream 103 in a countercurrent manner under conditions effective to saturate or increase the water content of the desulfurized feed stream 103. Saturation of the feed stream 101 is particularly beneficial if the reforming unit 104 implements a steam reforming process as a water-containing or saturated desulfurized feed stream 103 may be necessary in order for the steam reforming process to convert the desulfurized feed stream 103 to syngas in syngas stream 105. Additionally or alternatively, water may be injected directly into the reforming unit 104, particularly if the reforming unit 104 provides a steam reforming process. Syngas stream 105 is directed to a compression zone 106, which compresses syngas stream 105 in one or more stages to form compressed stream 107. Preferably, the compression zone 106 includes one or more centrifugal compressors. Compressed stream 107 is then directed to a methanol synthesis unit 108, wherein the syngas in compressed stream 107 contacts a methanol synthesis catalyst under conditions effective to convert at least a portion of the syngas to crude methanol in crude methanol stream 109. Optionally, unreacted syngas from methanol synthesis unit 108 is separated and recycled to compression zone 106 as shown by unreacted syngas stream 1 17.

The crude methanol in crude methanol stream 109 includes light ends, methanol, water, and fusel oil. Preferably, prior to introduction into separation zone 119, the crude methanol stream 109 is treated with a caustic medium, not shown, in a caustic wash unit, not shown, under conditions effective to increase the pH of the crude methanol stream 109. As a result, the crude methanol stream 109 also optionally includes dissolved caustic salts. Crude methanol stream 109 is directed to a separation zone 119, which is adapted to separate one or more of these components and isolate a relatively pure methanol stream. The separation zone 119 includes a light ends separation unit 110, such as a topping column, and a refining column 112. Crude methanol stream 109 is first directed to the light ends separation unit 110, wherein conditions are effective to separate the crude methanol stream 109 into light ends stream 118 and bottoms crude methanol stream 111, which may contain one or more of methanol, water, dissolved caustic salts and fusel oil. The light ends separation unit 110 typically includes from about 50 to about 80 or more trays and has a cross-sectional diameter of from about 8 feet (2.4 m) to about 20 or more feet (6 m). Preferably, light ends stream 118 contains a majority of the methane and carbon monoxide that was present in the crude methanol stream 109. At least a portion of the light ends stream 118 preferably is recycled to methanol synthesis unit 108, as shown, for further conversion to methanol while the bottoms crude methanol stream 111 is directed to refining column 112 for further processing. In refining column 112 the bottoms crude methanol stream 111 is subjected to conditions effective to separate the bottoms crude methanol stream 111 into a refined methanol stream 113, a fusel oil stream 114, and a water stream 115. A majority of the caustic salts, if any, from bottoms crude methanol stream 111 are dissolved in water stream 115. Preferably, refined methanol stream 113 contains at least 80 weight percent, more preferably at least 90 weight percent and most preferably at least 95 weight percent methanol, based on the total weight of the refined methanol stream 113. Preferably, refined methanol stream 113 contains less than 0.25 weight percent, more preferably less than 1 weight percent and most preferably less than 5 weight percent water, based on the total weight of the refined methanol stream 113. The refining column 112 typically includes from about 80 to about 120 or more trays and has a cross-sectional diameter of from about 10 feet (3.0 m) to about 24 or more feet (7.2 m).

C. MTO Reaction Systems

The present invention provides for combining a methanol synthesis system with an MTO reaction system, which is discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene. A non-limiting list of preferable SAPO molecular sieve catalysts includes SAPO-17, SAPO-18, SAPO-34, SAPO-35, SAPO-44, the substituted forms thereof, and mixtures thereof.

Although the present application is specifically directed to combining a methanol synthesis system with an MTO reaction system, other synthesis systems-and oxygenate to olefin (OTO) systems could be combined in accordance with the present invention. For example, an ethanol synthesis system could be combined with an ethanol to olefin reaction system. The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment, the feedstock contains one or more oxygenates, more specifically, one or more organic compounds containing at least one oxygen atom. In a most preferred embodiment, the oxygenate in the feedstock is one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The various feedstocks discussed above, particularly a feedstock containing an oxygenate, more particularly a feedstock containing an alcohol, is converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or, alternatively, methanol-to-olefins (MTO). In an MTO process, typically an oxygenated feedstock, most preferably a methanol-containing feedstock, is converted in the presence of a molecular sieve catalyst composition into one or more olefins, preferably and predominantly, ethylene and/or propylene, referred to herein as light olefins. Preferably, at least 90 weight percent, more preferably at least 95 weight percent, and most preferably at least 99 weight percent of the methanol in the feedstock is converted to light olefins, based on the total weight of the methanol in the feedstock.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous-high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type is any of the riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents fed to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1, preferably the WHSV for conversion of a feedstock containing methanol, DME, or both, is in the range of from about 20 hr-1 to about 300 hr-1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

Figure 2:
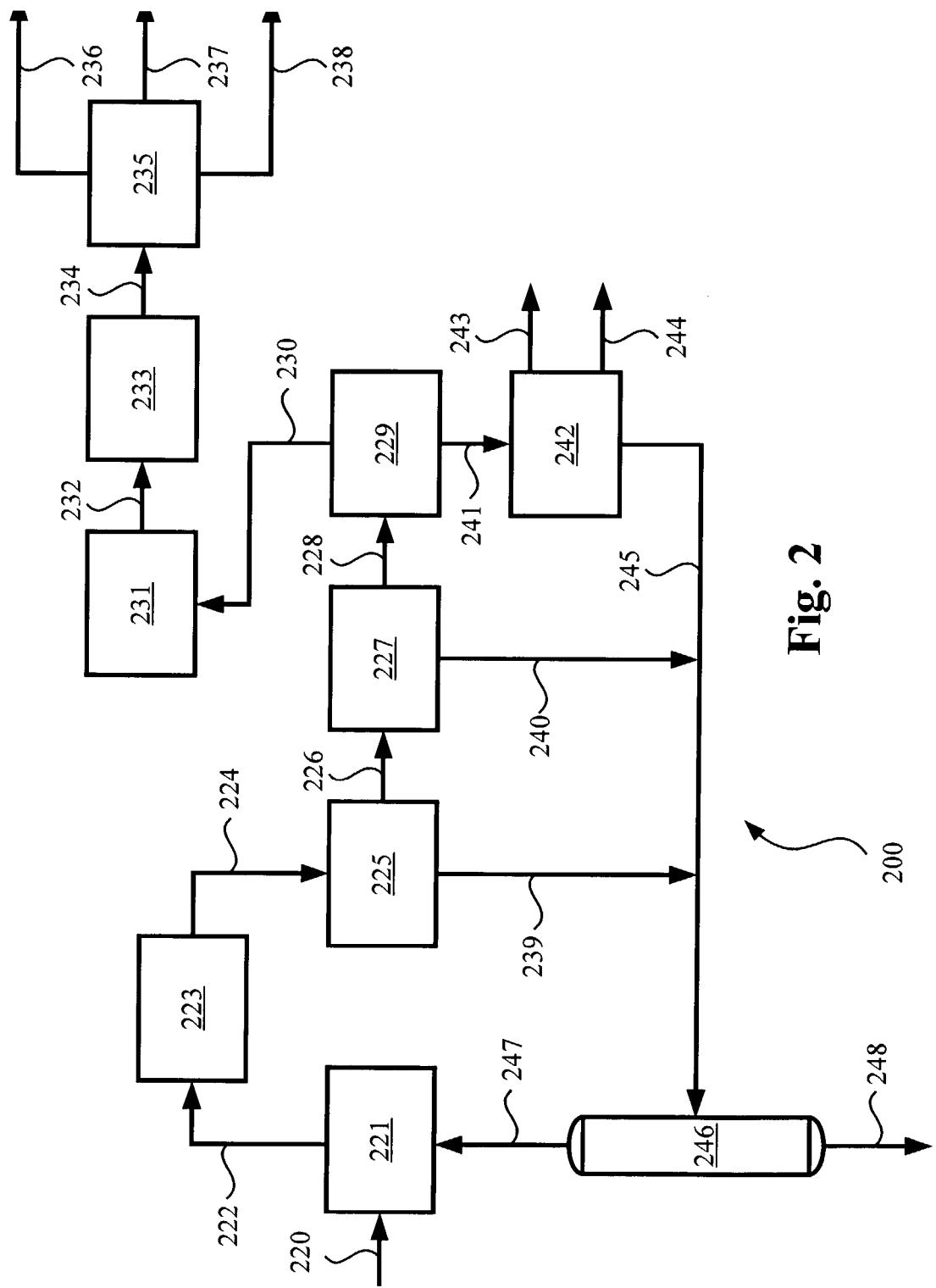
FIG. 2 is a flow diagram of a methanol-to-olefin reaction system.

FIG. 2 is a flow diagram illustrating an MTO reaction system, generally designated 200, and will now be described in greater detail. A methanol-containing feedstock or feed stream 220 is fed to a feed vaporization and introduction (FVI) system 221, which subjects the methanol in the methanol-containing feed stream 220 to conditions, e.g., heat and pressure, sufficient to at least partially vaporize the methanol. For example, the FVI system preferably includes a vapor-liquid disengaging drum, in which conditions are sufficient to provide a vaporized methanol-containing stream 222 and a liquid stream, not shown, which may include non-volatiles. The vaporized methanol-containing stream 222 is directed to MTO reactor unit 223, in which the methanol in vaporized methanol-containing stream 222 contacts an MTO catalyst under conditions effective to convert at least a portion of the methanol to light olefins in product stream 224. Product stream 224 includes methane, ethylene, ethane, propylene, propane, DME, C4 olefins, C5+ hydrocarbons, water and other hydrocarbon components.

The product stream 224 preferably is then directed to a quench unit 225, e.g., a quench tower, wherein the product stream 224 is cooled and water and other condensable components are condensed. The condensed components, which comprise a substantial amount of water, are withdrawn from the quench unit 225 through a quench bottoms stream 239. A portion of the condensed components are circulated through a recirculation line, not shown, back to the top of the quench unit 225. The recirculation line may contain a cooling unit, e.g., a heat exchanger, not shown, to further cool the condensed components so as to provide a cooling medium to further cool the components in quench unit 225.

Olefin vapor leaves through the overhead portion of quench unit 225 through quench overhead line 226. The olefin vapor in quench overhead line 226 is compressed in one or more stages and one or more compressors in compression zone 227 to form a compressed product stream 228. After each of one or more stages, the compressed stream passes through a heat exchanger, not shown, and is cooled in order to condense out heavier components such as residual water. The condensed component(s) are collected in one or more knock out drums, not shown, between compression stages and exit the compression zone 227 via compression condensate stream(s) 240. Compressed product stream 228 optionally passes through a water absorption unit, not shown, where methanol is preferably used as the water absorbent. In the water absorption unit, the water absorbent contacts the compressed product stream 228, preferably in a countercurrent manner, under conditions effective to separate water from the other components in the compressed product stream 228. The light olefins are recovered from the water absorption unit in an overhead stream, not shown. Optionally washed compressed product stream 228 is directed to a separation system for separating the various components contained therein.

A variety of separation systems may be implemented in accordance with the present invention. U.S. patent applications Ser. No. 10/125,138, filed Apr. 18, 2002, and Ser. No. 10/124,859, also filed Apr. 18, 2002, the entireties of which are incorporated herein by reference, describe two separation schemes which may be implemented in accordance with the present invention. One exemplary non-limiting separation system is illustrated in FIG. 2. As shown, compressed product stream 228 is directed to a C3− separation zone 229. The C3− separation zone 229 separates ethylene and propylene, as well as lighter components, from the DME and heavier components, including C4 olefins, C5+ hydrocarbons, unreacted methanol, and methanol remaining from the optional water absorption unit. The C3− separation zone 229 includes one or more separation units, e.g., distillation columns, which are adapted to separate C3− components from the DME and heavier components. Additional methanol, not shown, optionally is added to the C3− separation zone 229 to reduce hydrate and/or free water formation. A majority of the ethylene and propylene from compressed product stream 228 exits the C3− separation zone 229 via C3− overhead stream 230. A majority of the DME and heavier components, which include C4+ olefins and C5+ hydrocarbons, exits the C3− separation zone 229 through C4+ bottoms stream 241.

The C3− components in C3− overhead stream 230 preferably are directed to a caustic wash unit 231, in which the C3− overhead stream 230 contacts a caustic wash medium under conditions effective to remove carbon dioxide and carbonic acid therefrom and form $CO_2$ depleted stream 232. Preferably, the caustic wash medium is sent through a line, not shown, to the top portion of the caustic wash unit 231 to remove carbon dioxide, which is entrained in the C3− overhead stream 230. Spent caustic leaves the caustic wash unit 231 through a waste caustic line, not shown.

Caustic treated ethylene and propylene exits caustic wash unit 231 through $CO_2$ depleted stream 232 and preferably is directed to a water wash column, not shown, and/or to drying section 233. Water enters the water wash column and water and absorbed components exit the water wash column through a bottoms line, not shown. Water washed ethylene and propylene exit the water wash column through an overhead line, not shown, and pass through a drying section 233. Dry product stream 234 preferably contains less than 5 weight percent water, more preferably less than 1 weight percent water, and most preferably less than 0.5 weight percent water, based on the total weight of the dry methanol stream 234. Dry product stream 234 exits the drying section 233 and is directed to a C2/C3 separation system 235, which preferably includes one or more cryogenic fractionation columns. The C2/C3 separation system 235 preferably forms a tail gas stream 236, an ethylene product stream 237, and a propylene product stream 238. The tail gas stream 236 preferably includes the majority of the methane and hydrogen that was present in the dry product stream 234; the ethylene product stream 237 preferably includes a majority of the ethylene that was present in the dry product stream 234; and the propylene product stream 238 preferably includes a majority of the propylene that was present in the dry product stream 234. The ethylene and/or propylene in the ethylene product stream 237 and propylene product stream 238 may be used as monomers or comonomers for the formation of polyethylene and/or polypropylene. The tail gas stream 236 optionally is burned as a fuel in one or more of the steps of the MTO reaction process.

C4+ bottoms stream 241 from C3− separation zone 229 is directed to a C4/C5+ separation zone 242. The C4/C5+ separation zone 242 includes one or more separation devices, e.g., distillation towers, which separate the C4 olefins from C5+ hydrocarbons in the C4+ bottoms stream 241, thereby forming C4 product stream 243 and C5+ product stream 244. The C4/C5+ separation zone 242 also forms a methanol-containing stream 245, which preferably includes water, unreacted methanol from the vaporized methanol-containing stream 222, methanol from an upstream water absorption unit, if any, DME, and other oxygenate components. Ideally, methanol-containing stream 245 includes a majority of the methanol and water that was present in the C4+ bottoms stream 241.

As shown, methanol-containing stream 245 is directed to a methanol/water separation unit 246. Additionally or alternatively, quench tower bottoms stream 239 and/or compressor condensate stream(s) 240, alone or in combination, are directed to the methanol/water separation unit 246. Optionally, quench bottoms stream 239 and compressor condensate stream(s) 240 are combined with methanol-containing stream 245 and directed to the methanol/water separation unit 246 in a single line, as illustrated in FIG. 2. The methanol/water separation unit 246 preferably includes one or more separation devices, e.g., distillation towers, which subject the methanol containing stream 245 to conditions effective to separate the methanol and oxygenated hydrocarbon byproducts from the water in one or more of the quench bottoms stream 239, compressor condensate stream(s) 240 and methanol-containing stream 245. The methanol/water separation unit 246 thus forms an overhead oxygenate stream 247, which includes a majority of the methanol that was present in the one or more stream(s) that were directed to the methanol/water separation unit 246. Preferably, at least a portion of the overhead oxygenate stream 247 is redirected to the FVI system 221 for vaporization, introduction into MTO reactor unit 223, and conversion to light olefins. The methanol/water separation unit 246 also forms a water stream 248 which includes a majority of the water that was present in the one or more stream(s) that were directed to the methanol/water separation unit 246. The methanol/water separation unit 246 typically includes from about 50 to about 80 or more trays and has a cross-sectional diameter of from about 10 feet (3 m) to about 20 or more feet (6 m).

D. Integrated Methanol/MTO Reaction System

In accordance with the present invention, a methanol synthesis system is integrated with an MTO reaction system. Specifically, the methanol/water separation unit 246 of the MTO reaction system 200 also receives the crude methanol stream 109 from methanol synthesis system 100. That is, the methanol synthesis system and the MTO reaction system share a common separation device or devices, thereby eliminating one or more separation devices from the integrated system.

Figure 3:
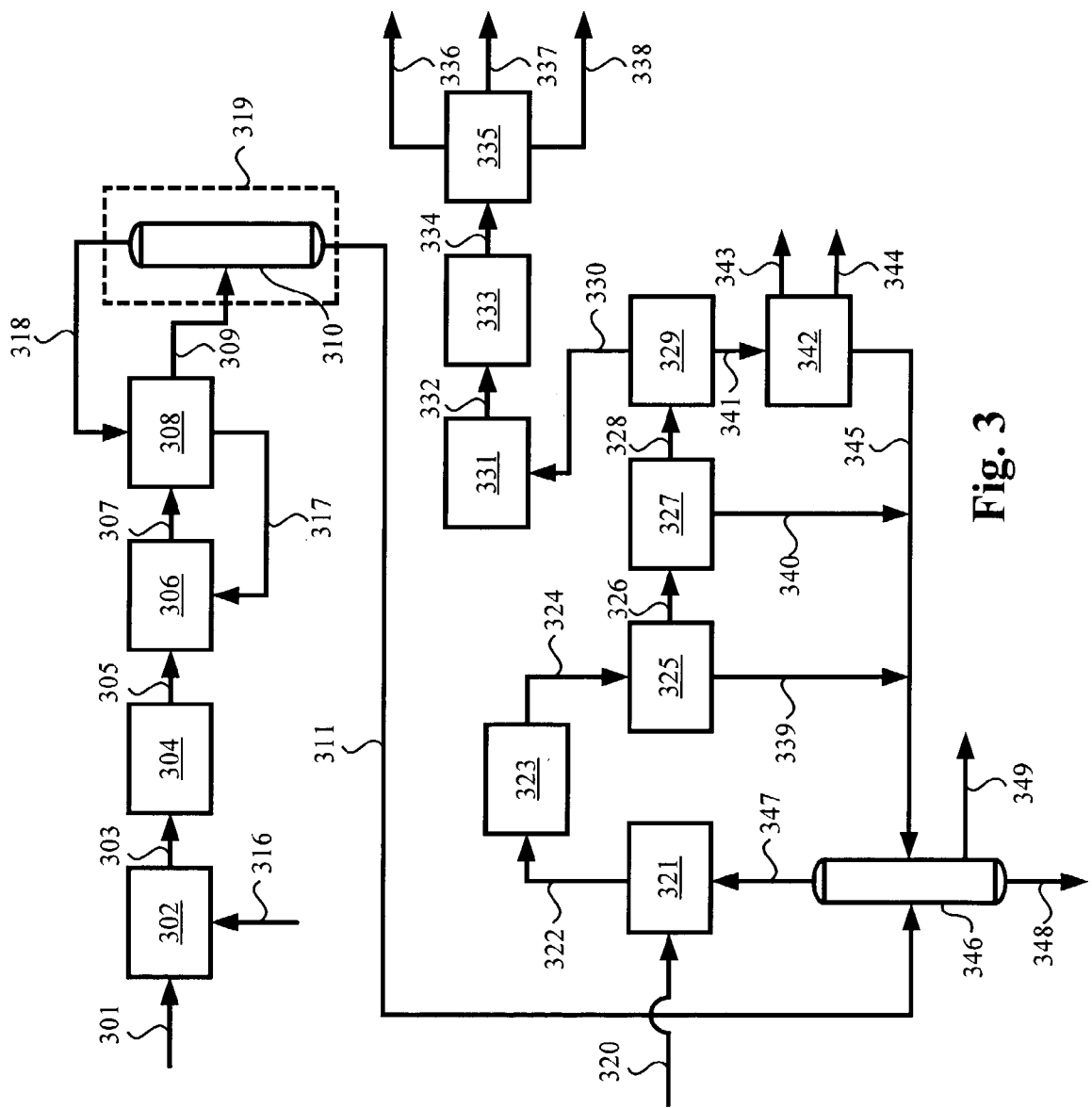
FIG. 3 is a flow diagram of an integrated methanol synthesis and methanol-to-olefin reaction system.

FIG. 3 illustrates a non-limiting integrated system in accordance with one embodiment of the present invention. In this integrated system, the methanol/water separation unit 346 of the integrated system substantially performs the function of the refining column 112 in FIG. 1.

As shown in FIG. 3, a feed stream 301, which preferably includes natural gas, is directed to a desulfurization unit 302. Prior to entering the desulfurization unit 302, the feed stream 301 optionally is compressed by one or more compressors, not shown, to facilitate movement of the feed stream 301 and various intermediate streams through the methanol synthesis system. In one embodiment, the natural gas from feed stream 301 contacts water from water stream 316 in the desulfurization unit 302 in a countercurrent manner under conditions effective to remove sulfur-containing components therefrom. In this manner, the desulfurization unit 302 acts as an absorption unit. Additionally or alternatively, the desulfurization unit 302 may act as an adsorption unit, as described above. If the desulfurization unit 302 includes an adsorption unit, the feed stream 301 preferably is heated to a temperature of between 700° F. (371° C.) and 800° F. (427° C.) by a heat exchanger, not shown, before it is directed to desulfurization unit 302. The desulfurization unit 302 forms desulfurized feed stream 303, which is directed to a reforming unit 304.

The reforming unit 304 converts the natural gas in desulfurized feed stream 303 to syngas in syngas stream 305. The reforming unit 304 may be a steam reforming unit, a partial oxidation unit, an autothermal reforming unit, and/or a combined reforming unit, e.g., a unit that combines two or more of these reforming processes. In one embodiment, water from water stream 316 preferably increases the water content of, and more preferably saturates, the feed stream 301, in the process of removing sulfur-containing components. Additionally or alternatively, the desulfurized feed stream 303 is directed to a separate saturization unit, not shown, in which water contacts the desulfurized feed stream 303 under conditions effective to saturate the desulfurized feed stream 303 or increase the water content thereof. Additionally or alternatively, water may be injected directly into the reforming unit 304, particularly if the reforming unit 304 provides a steam reforming process. Syngas stream 305 is directed to a compression zone 306, which compresses syngas stream 305 in one or more stages to form compressed stream 307. Preferably, the compression zone 306 includes one or more centrifugal compressors. Compressed stream 307 is then directed to a methanol synthesis unit 308, wherein the syngas in compressed stream 307 contacts a methanol synthesis catalyst under conditions effective to convert at least a portion of the syngas to crude methanol in crude methanol stream 309. Optionally, unreacted syngas from methanol synthesis unit 308 is separated and recycled to compression zone 306 as shown by unreacted syngas stream 317.

The crude methanol in crude methanol stream 309 includes light ends, methanol, water, and fusel oil. Preferably, prior to introduction into separation zone 319, the crude methanol stream 309 is treated with a caustic medium, not shown, in a caustic wash unit, not shown, under conditions effective to increase the pH of the crude methanol stream 309. As a result, the crude methanol stream 309 also optionally includes dissolved caustic salts. Crude methanol stream 309 is directed to a separation zone 319. In the embodiment illustrated in FIG. 3, the separation zone 319 removes light ends from the crude methanol stream 309. The separation zone 319 includes a light ends separation unit 310, such as a topping column. Crude methanol stream 309 is first directed to the light ends separation unit 310, wherein conditions are effective to separate the crude methanol stream 309 into light ends stream 318 and bottoms crude methanol stream 311, which may contain one or more of methanol, water, dissolved caustic salts and fusel oil. The light ends separation unit 310 typically includes from about 40 to about 70 or more trays and has a cross-sectional diameter of from about 6 feet (1.8 m) to about 16 or more feet (4.8 m). Preferably, light ends stream 318 contains a majority of the methane and carbon monoxide that was present in the crude methanol stream 309. At least a portion of the light ends stream 318 preferably is recycled to methanol synthesis unit 308, as shown, for further conversion to methanol while the bottoms crude methanol stream 311 is directed to the integrated methanol/water separation unit 346 for further processing, rather than being directed to a conventional refining column.

Unlike the separation system 119 illustrated in FIG. 1, the methanol synthesis system shown in FIG. 3 does not include a refining column that is dedicated exclusively to receiving and processing crude methanol from the methanol synthesis system. Instead, the bottoms crude methanol stream 311 is directed to the integrated methanol/water separation unit 346, which may be semantically referred to as a distillation or refining column, but which receives streams from both the methanol synthesis system and the MTO reaction system. In the methanol/water separation unit 346 the bottoms crude methanol stream 311 is subjected to conditions effective to separate the bottoms crude methanol stream 311 into oxygenate stream 347, a fusel oil stream 349, and a water stream 348. A majority of the caustic salts, if any, from bottoms crude methanol stream 311 are dissolved in water stream 348. Preferably, oxygenate stream 347 contains at least 80 weight percent, preferably at least 90 weight percent and most preferably at least 95 weight percent methanol, based on the total weight of the oxygenate stream 347. Preferably, oxygenate stream 347 contains less than 25 weight percent, more preferably less than 10 weight percent and most preferably less than 5 weight percent water, based on the total weight of the oxygenate stream 347. In terms of lower range limits, oxygenate stream 347 optionally contains more than 0.25 weight percent, more than 1 weight percent or more than 5 weight percent water, based on the total weight of the oxygenate stream 347. The integrated methanol/water separation unit 346 preferably includes from about 50 to about 80 or more trays and has a cross-sectional diameter of from about 10 feet (3 m) to about 20 or more feet (6 m). The integrated methanol/water separation unit 346 preferably has about the same number of trays as the methanol/water separation unit 246 in a non-integrated MTO reaction system. However, the integrated methanol/water separation 346 unit preferably has a larger cross-sectional diameter than the non-integrated methanol/water separation unit 246 in order to accommodate the increased volume of material that is processed thereby.

Thus, the present invention provides the additional advantage in that the integrated methanol/water separation unit 346, which preferably includes about 65 trays, has a height which is less than the height of the refining column 112, which typically has about 110 trays, in a separate methanol synthesis system. That is, the present invention not only provides for a reduction in the quantity of individual separation units, but the integrated separation unit of the present invention can be of a smaller size than the largest separation unit in a non-integrated methanol synthesis system. Although a slight decrease in methanol purity is realized by the decrease in number of trays over a conventional methanol synthesis refining column, it has been discovered that this decreased purity of the integrated system does not significantly affect the efficiency or operability of the MTO reaction process.

A methanol-containing feedstock or feed stream 320 optionally is fed to a feed vaporization and introduction (FVI) system 321, which subjects the methanol in the methanol-containing feed stream 320 to conditions, e.g., heat and pressure, sufficient to at least partially vaporize the methanol. The feed stream 320 is optional in the integrated system because the FVI system 321 of the integrated system receives methanol from the methanol synthesis system via methanol/water separation unit 346 and oxygenate stream 347. The FVI system 321 preferably includes a vapor-liquid disengaging drum, in which conditions are sufficient to provide a vaporized methanol-containing stream 322 and a liquid stream, not shown, which may include non-volatiles. The vaporized methanol-containing stream 322 is directed to MTO reactor unit 323, in which the methanol in vaporized methanol-containing stream 322 contacts an MTO catalyst under conditions effective to convert at least a portion of the methanol to light olefins in product stream 324. Product stream 324 preferably includes methane, ethylene, ethane, propylene, propane, DME, C4 olefins, C5+ hydrocarbons, water and other hydrocarbon components.

The product stream 324 preferably is then directed to a quench unit 325, e.g., a quench tower, wherein the product stream 324 is cooled and water and other condensable components are condensed. The condensed components, which comprise a substantial amount of water, are withdrawn from the quench unit 325 through a quench bottoms stream 339. A portion of the condensed components are circulated through a recirculation line, not shown, back to the top of the quench unit 325. The recirculation line may contain a cooling unit, e.g., a heat exchanger, not shown, to further cool the condensed components so as to provide a cooling medium to further cool the components in quench unit 325.

Olefin vapor leaves through the overhead portion of quench unit 325 through quench overhead line 326. The olefin vapor in quench overhead line 326 is compressed in one or more stages and one or more compressors in compression zone 327 to form a compressed product stream 328. After each of one or more stages, the compressed stream passes through a heat exchanger, not shown, and is cooled in order to condense out heavier components such as residual water. The condensed component(s) are collected in one or more knock out drums, not shown, between compression stages and exit the compression zone 327 via one or more compression condensate stream(s) 340. Compressed product stream 328 optionally passes through a water absorption unit, not shown, where methanol is preferably used as the water absorbent. In the water absorption unit, the water absorbent contacts the compressed product stream 328, preferably in a countercurrent manner, under conditions effective to separate water from the other components in the compressed product stream 328. The light olefins are recovered from the water absorption unit in an overhead stream, not shown. Optionally washed compressed product stream 328 is directed to a separation system for separating the various components contained therein.

As discussed above, a variety of separation systems may be implemented in the integrated system in accordance with the present invention. One exemplary non-limiting separation system is illustrated in FIG. 3. As shown, compressed product stream 328 is directed to a C3− separation zone 329. The C3− separation zone 329 separates ethylene and propylene, as well as lighter components, from the DME and heavier components, including C4 olefins, C5+ hydrocarbons, unreacted methanol, and methanol remaining from the optional water absorption unit. The C3− separation zone 329 includes one or more separation units, e.g., distillation columns, which are adapted to separate C3− components from the DME and heavier components. Additional methanol, not shown, optionally is added to the C3− separation zone 329 to reduce hydrate and/or free water formation. A majority of the ethylene and propylene from compressed product stream 328 exits the C3− separation zone 329 via C3− overhead stream 330. A majority of the DME and heavier components, which include C4 olefins and C5+ hydrocarbons, exits the C3− separation zone 329 through C4+ bottoms stream 341.

The C3− components in C3− overhead stream 330 preferably are directed to a caustic wash unit 331, in which the C3− overhead stream 330 contacts a caustic wash medium under conditions effective to remove carbon dioxide and carbonic acid therefrom and form $CO_2$ depleted stream 332. Preferably, the caustic wash medium is sent through a line, not shown, to the top portion of the caustic wash unit 331 to remove carbon dioxide, which is entrained in the C3− overhead stream 330. Spent caustic leaves the caustic wash unit 331 through a waste caustic line, not shown.

Caustic treated ethylene and propylene exits caustic wash unit 331 through $CO_2$ depleted stream 332 and preferably is directed to a water wash column, not shown, and/or to drying section 333. Water enters the water wash column and water and absorbed components exit the water wash column through a bottoms line, not shown. Water washed ethylene and propylene exit the water wash column through an overhead line, not shown, and pass through a drying section 333. Dry product stream 334 exits the drying section 333 and is directed to a C2/C3 separation system 335, which preferably includes one or more cryogenic fractionation columns. Dry product stream 334 preferably contains less than 5 weight percent water, more preferably less than 1 weight percent water, and most preferably less than 0.5 weight percent water, based on the total weight of the dry methanol stream 334. The C2/C3 separation system 335 preferably forms a tail gas stream 336, an ethylene product stream 337, and a propylene product stream 338. The tail gas stream 336 preferably includes the majority of the methane and hydrogen that was present in the dry product stream 334; the ethylene product stream 337 preferably includes a majority of the ethylene that was present in the dry product stream 334; and the propylene product stream 338 preferably includes a majority of the propylene that was present in the dry product stream 334. The ethylene and/or propylene in the ethylene product stream 337 and propylene product stream 338 may be used as monomers or comonomers for the formation of polyethylene and/or polypropylene. The tail gas stream 336 optionally is burned as a fuel in one or more of the steps of the MTO reaction process.

C4+ bottoms stream 341 from C3− separation zone 329 is directed to a C4/C5+ separation zone 342. The C4/C5+ separation zone 342 includes one or more separation devices, e.g., distillation towers, which separate the C4 olefins from C5+ hydrocarbons in the C4+ bottoms stream 341, thereby forming C4 product stream 343 and C5+ product stream 344. The C4/C5+ separation zone 342 also forms a methanol-containing stream 345, which preferably includes water, unreacted methanol from the vaporized methanol-containing stream 322, methanol from an upstream water absorption unit, if any, DME, and other oxygenate components. Ideally, methanol-containing stream 345 includes a majority of the methanol and water that was present in the C4+ bottoms stream 341.

As shown, methanol-containing stream 345, in addition to bottoms crude methanol stream 311, is directed to the methanol/water separation unit 346. Additionally or alternatively, quench tower bottoms stream 339 and/or compressor condensate stream(s) 340, alone or in combination, are directed to the methanol/water separation unit 346. Optionally, quench bottoms stream 339 and compressor condensate stream(s) 340 are combined with methanol-containing stream 345 and directed to the methanol/water separation unit 346 in a single line, as illustrated in FIG. 3. The methanol/water separation unit 346 preferably includes one or more separation devices, e.g., distillation towers, which subject the methanol-containing stream 345 to conditions effective to separate the methanol from the fusel oil and water in one or more of the quench bottoms stream 339, compressor condensate stream(s) 340 and methanol-containing stream 345. The methanol/water separation unit 346 thus forms an overhead oxygenate stream 347, which includes a majority of the methanol that was present in the one or more stream(s) that were directed to the methanol/water separation unit 346. Ideally, the one or more streams that are directed to the methanol/water separation unit 346, e.g., at least a portion of the effluent stream, contain at least 0.5 weight percent methanol, more preferably at least 2 weight percent methanol, more preferably at least 5 weight percent methanol, and most preferably at least 20 weight percent methanol, based on the total weight of the one or more streams. The one or more streams that are directed to the methanol/water separation unit 346 also preferably contain less than 50 weight percent light olefins, more preferably less than 30 weight percent light olefins, and most preferably less than 10 weight percent light olefins, based on the total weight of the one or more streams. Preferably, at least a portion of the overhead oxygenate stream 347 is redirected to the FVI system 321 for vaporization, introduction into MTO reactor unit 323, and conversion to light olefins. The methanol/water separation unit 346 also forms a water stream 348, which includes a majority of the water that was present in the one or more streams that were directed to the methanol/water separation unit 346.

Figure 4:
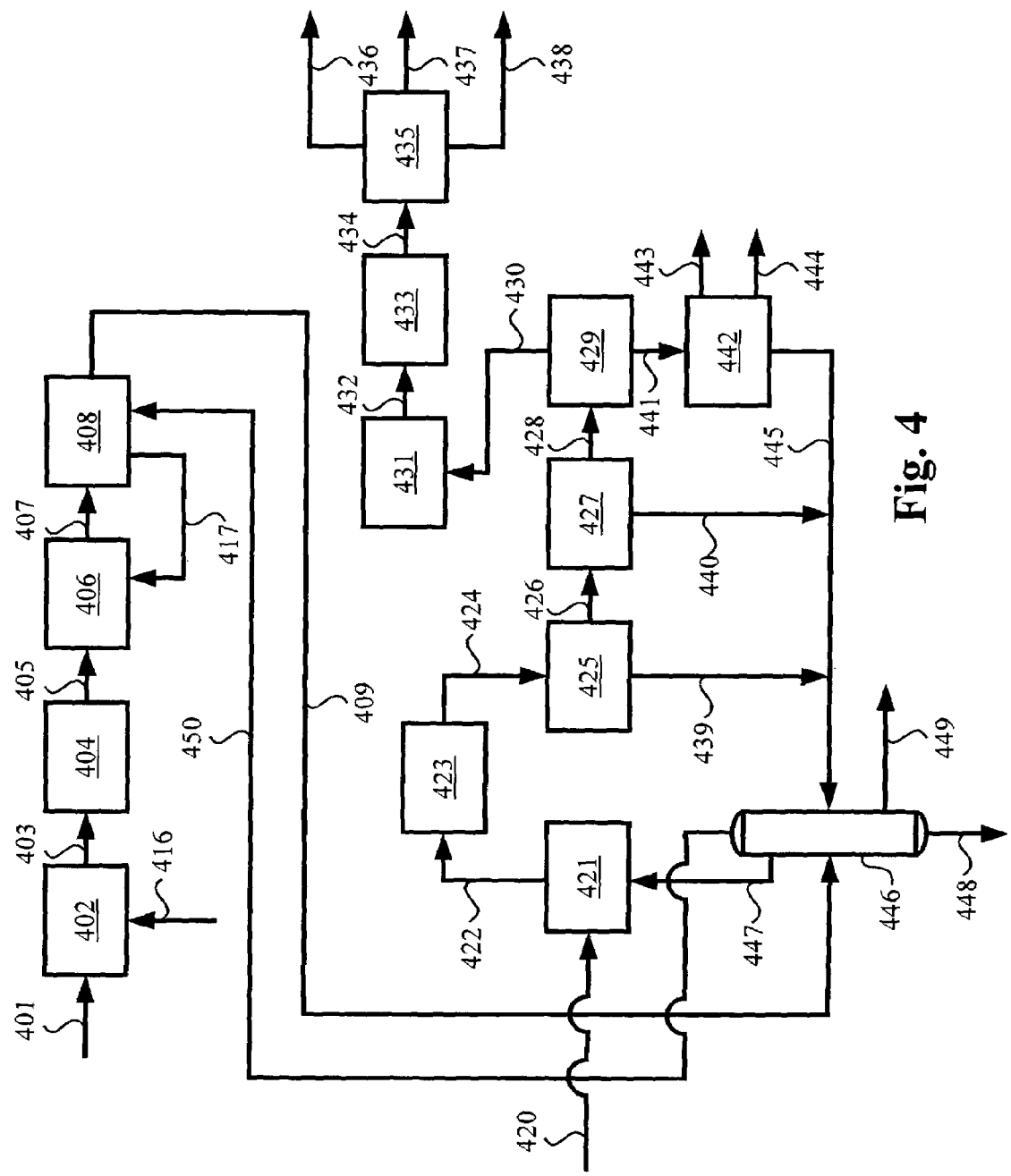
FIG. 4 is a flow diagram of an integrated methanol synthesis and methanol-to-olefin reaction system.

FIG. 4 illustrates another non-limiting integrated system in accordance with one embodiment of the present invention. In this integrated system, the methanol/water separation unit 446 of the integrated system substantially performs the function of the light ends separation unit 110 and the refining column 112 in the methanol synthesis system 100 illustrated in FIG. 1.

As shown in FIG. 4, a feed stream 401, which preferably includes natural gas, is directed to a desulfurization unit 402. Prior to entering the desulfurization unit 402, the feed stream 401 optionally is compressed by one or more compressors to facilitate movement of the feed stream 401 and various intermediate streams through the methanol synthesis system. In one embodiment, the natural gas from feed stream 401 contacts water from water stream 416 in the desulfurization unit 402 in a countercurrent manner under conditions effective to remove sulfur-containing components therefrom. In this manner, the desulfurization unit 402 acts as an absorption unit. Additionally or alternatively, the desulfurization unit 402 may act as an adsorption unit, as described above. If the desulfurization unit 402 includes an adsorption unit, the feed stream 401 preferably is heated to a temperature of between 700° F. (371° C.) and 800° F. (427° C.) by a heat exchanger, not shown, before it is directed to desulfurization unit 402. The desulfurization unit 402 forms desulfurized feed stream 403, which is directed to a reforming unit 404.

The reforming unit 404 converts the natural gas in desulfurized feed stream 403 to syngas in syngas stream 405. The reforming unit 404 may be a steam reforming unit, a partial oxidation unit, an autothermal reforming unit, and/or a combined reforming unit, e.g., a unit that combines two or more of these reforming processes. In one embodiment, water from water stream 416 preferably increases the water content of, and more preferably saturates, the feed stream 401, in the process of removing sulfur-containing components. Additionally or alternatively, the desulfurized feed stream 403 is directed to a separate saturation unit, not shown, in which water contacts the desulfurized feed stream 403 under conditions effective to saturate the desulfurized feed stream 403 or increase the water content thereof. Additionally or alternatively, water may be injected directly into the reforming unit 404, particularly if the reforming unit 404 provides a steam reforming process. Syngas stream 405 is directed to a compression zone 406, which compresses syngas stream 405 in one or more stages to form compressed stream 407. Preferably, the compression zone 406 includes one or more centrifugal compressors. Compressed stream 407 is then directed to a methanol synthesis unit 408, wherein the syngas in compressed stream 407 contacts a methanol synthesis catalyst under conditions effective to convert at least a portion of the syngas to crude methanol in crude methanol stream 409. Optionally, unreacted syngas from methanol synthesis unit 408 is separated and recycled to compression zone 406 as shown by unreacted syngas stream 417.

The crude methanol in crude methanol stream 409 includes light ends, methanol, water, and fusel oil. Preferably, the crude methanol stream 409 is treated with a caustic medium, not shown, in a caustic wash unit, not shown, under conditions effective to increase the pH of the crude methanol stream 409. As a result, the crude methanol stream 409 also optionally includes dissolved caustic salts.

Unlike the separation system 119 illustrated in FIG. 1, the methanol synthesis system shown in FIG. 4 does not include either a light ends separation unit or a refining column that is dedicated exclusively to receiving and processing crude methanol from the methanol synthesis system. Instead, the crude methanol stream 409 is directed to an integrated methanol/water separation unit 446. In the integrated methanol/water separation unit 446 the crude methanol stream 409 (and any other streams directed to the integrated methanol/water separation unit 446) is subjected to conditions effective to separate the crude methanol stream 409 into a light ends stream 450, an oxygenate side stream 447, a fusel oil stream 449, and a water stream 448. Preferably, light ends stream 450 contains a majority if the methane and carbon monoxide that was present in the crude methanol stream 409. At least a portion of the light ends stream 450 preferably is recycled to methanol synthesis unit 408, as shown, for further conversion to methanol. A majority of the caustic salts, if any, from crude methanol stream 409 are dissolved in water stream 448.

Preferably, oxygenate side stream 447 contains at least 80 weight percent, more preferably at least 90 weight percent and most preferably at least 95 weight percent methanol, based on the total weight of the oxygenate side stream 447. Preferably, oxygenate side stream 447 contains less than 25 weight percent, more preferably less than 10 weight percent and most preferably less than 5 weight percent water, based on the total weight of the oxygenate side stream 447. In terms of lower range limits, oxygenate side stream 447 optionally contains more than 0.25 weight percent, more than 1 weight percent, or more than 5 weight percent water, based on the total weight of the oxygenate side stream 447. The integrated methanol/water separation unit 446 preferably includes from about 50 to about 80 or more trays and has a cross-sectional diameter of greater than from about 10 feet (3 m) to about 20 or more feet (6 m).

Thus, as with the previously discussed embodiment, the present invention provides the additional advantage in that the integrated methanol/water separation unit 446, which includes about 65 trays, has a height which is less than the height of the refining column 112 in a separate methanol synthesis system, which typically includes about 110 trays. That is, the present invention not only provides for a reduction in the quantity of individual separation units, but the integrated separation unit of the present invention optionally is of a smaller size than the largest separation unit in a non-integrated system.

A methanol-containing feedstock or feed stream 420 optionally is fed to a feed vaporization and introduction (FVI) system 421, which subjects the methanol in the methanol-containing feed stream 420 to conditions, e.g., heat and pressure, sufficient to at least partially vaporize the methanol. The feed stream 420 is optional in the integrated system because the FVI system 421 of the integrated system receives methanol from the methanol synthesis system via methanol/water separation unit 446 and oxygenate side stream 447. The FVI system 421 preferably includes a vapor-liquid disengaging drum, in which conditions are sufficient to provide a vaporized methanol-containing stream 422 and a liquid stream, not shown, which may include non-volatiles. The vaporized methanol-containing stream 422 is directed to MTO reactor unit 423, in which the methanol in vaporized methanol-containing stream 422 contacts an MTO catalyst under conditions effective to convert at least a portion of the methanol to light olefins in product stream 424. Product stream 424 preferably includes methane, ethylene, ethane, propylene, propane, DME, C4 olefins, C5+ hydrocarbons, water and other hydrocarbon components.

The product stream 424 preferably is then directed to a quench unit 425, e.g., a quench tower, wherein the product stream 424 is cooled and water and other condensable components are condensed. The condensed components, which comprise a substantial amount of water, are withdrawn from the quench unit 425 through a quench bottoms stream 439. A portion of the condensed components are circulated through a recirculation line, not shown, back to the top of the quench unit 425. The recirculation line may contain a cooling unit, e.g., a heat exchanger, not shown, to further cool the condensed components so as to provide a cooling medium to further cool the components in quench unit 425.

Olefin vapor leaves through the overhead portion of quench unit 425 through quench overhead line 426. The olefin vapor in quench overhead line 426 is compressed in one or more stages and one or more compressors in compression zone 427 to form a compressed product stream 428. After each of one or more stages, the compressed stream passes through a heat exchanger, not shown, and is cooled in order to condense out heavier components such as residual water. The condensed component(s) are collected in one or more knock out drums, not shown, between compression stages and exit the compression zone 427 via one or more compression condensate stream(s) 440. Compressed product stream 428 optionally passes through a water absorption unit, not shown, where methanol is preferably used as the water absorbent. In the water absorption unit, the water absorbent contacts the compressed product stream 428, preferably in a countercurrent manner, under conditions effective to separate water from the other components in the compressed product stream 428. The light olefins are recovered from the water absorption unit in an overhead stream, not shown. Optionally washed compressed product stream 428 is directed to a separation system for separating the various components contained therein.

As discussed above, a variety of separation systems may be implemented in the integrated system in accordance with the present invention. One exemplary non-limiting separation system is illustrated in FIG. 4. As shown, compressed product stream 428 is directed to a C3– separation zone 429. The C3– separation zone 429 separates ethylene and propylene, as well as lighter components, from the DME and heavier components, including C4 olefins, C5+ hydrocarbons, unreacted methanol, and methanol remaining from the optional water absorption unit. The C3– separation zone 429 includes one or more separation units, e.g., distillation columns, which are adapted to separate C3– components from the DME and heavier components. Additional methanol, not shown, optionally is added to the C3– separation zone 429 to reduce hydrate and/or free water formation. A majority of the ethylene and propylene from compressed product stream 428 exits the C3– separation zone 429 via C3– overhead stream 430. A majority of the DME and heavier components, which include C4+ olefins and C5+ hydrocarbons, exits the C3– separation zone 429 through C4+ bottoms stream 441.

The C3– components in C3– overhead stream 430 preferably are directed to a caustic wash unit 431, in which the C3– overhead stream 430 contacts a caustic wash medium under conditions effective to remove carbon dioxide and carbonic acid therefrom and form $CO_2$ depleted stream 432. Preferably, the caustic wash medium is sent through a line, not shown, to the top portion of the caustic wash unit 431 to remove carbon dioxide, which is entrained in the C3– overhead stream 430. Spent caustic leaves the caustic wash unit 431 through a waste caustic line, not shown.

Caustic treated ethylene and propylene exits caustic wash unit 431 through $CO_2$ depleted stream 432 and preferably is directed to a water wash column, not shown, and/or to drying section 433. Water enters the water wash column and water and absorbed components exit the water wash column through a bottoms line, not shown. Water washed ethylene and propylene exit the water wash column through an overhead line, not shown, and pass through a drying section 433. Dry product stream 434 exits the drying section 433 and is directed to a C2/C3 separation system 435, which preferably includes one or more cryogenic fractionation columns. Dry product stream 434 preferably contains less than 5 weight percent water, more preferably less than 1 weight percent water, and most preferably less than 0.5 weight percent water, based on the total weight of the dry methanol stream 434. The C2/C3 separation system 435 preferably forms a tail gas stream 436, an ethylene product stream 437, and a propylene product stream 438. The tail gas stream 436 preferably includes the majority of the methane and hydrogen that was present in the dry product stream 434; the ethylene product stream 437 preferably includes a majority of the ethylene that was present in the dry product stream 434; and the propylene product stream 438 preferably includes a majority of the propylene that was present in the dry product stream 434. The ethylene and/or propylene in the ethylene product stream 437 and propylene product stream 438 may be used as monomers or comonomers for the formation of polyethylene and/or polypropylene. The tail gas stream 436 optionally is burned as a fuel in one or more of the steps of the MTO reaction process.

C4+ bottoms stream 441 from C3– separation zone 429 is directed to a C4/C5+ separation zone 442. The C4/C5+ separation zone 442 includes one or more separation devices, e.g., distillation towers, which separate the C4 olefins from C5+ hydrocarbons in the C4+bottoms stream 441, thereby forming C4 product stream 443 and C5+ product stream 444. The C4/C5+ separation zone 442 also forms a methanol-containing stream 445, which preferably includes water, unreacted methanol from the vaporized methanol-containing stream 422, methanol from an upstream water absorption unit, if any, DME, and other oxygenate components. Ideally, methanol-containing stream 445 includes a majority of the methanol and water that was present in the C4+ bottoms stream 441.

As shown, methanol-containing stream 445, in addition to crude methanol stream 409, is directed to the methanol/water separation unit 446. Additionally or alternatively, quench tower bottoms stream 439 and/or compressor condensate stream(s) 440, alone or in combination, are directed to the methanol/water separation unit 446. Optionally, quench bottoms stream 439 and compressor condensate stream(s) 440 are combined with methanol-containing stream 445 and directed to the methanol/water separation unit 446 in a single line, as illustrated in FIG. 4. The methanol/water separation unit 446 preferably includes one or more separation devices, e.g., distillation towers, which subject the methanol-containing stream 445 to conditions effective to separate light ends and methanol from the fusel oil and water in one or more of the quench bottoms stream 439, compressor condensate stream(s) 440 and methanol-containing stream 445. The methanol/water separation unit 446 thus forms an oxygenate side stream 447, which includes a majority of the methanol that was present in the one or more streams that were directed to the methanol/water separation unit 446. Ideally, the one or more streams that are directed to the methanol/water separation unit 446, e.g., at least a portion of the effluent stream, contain at least 0.5 weight percent methanol, more preferably at least 2 weight percent methanol, more preferably at least 5 weight percent methanol, and most preferably at least 20 weight percent methanol, based on the total weight of the one or more streams. The one or more streams that are directed to the methanol/water separation unit 446 also preferably contain less than 50 weight percent light olefins, more preferably less than 30 weight percent light olefins, and most preferably less than 10 weight percent light olefins, based on the total weight of the one or more streams. Preferably, at least a portion of the oxygenate side stream 447 is redirected to the FVI system 421 for vaporization, introduction into MTO reactor unit 423, and conversion to light olefins. Optionally, oxygenate side stream 447 is sent directly to the MTO reactor 423, without passing through the FVI system. The methanol/water separation unit 446 also forms a water stream 448 which includes a majority of the water and caustic salts, if any, that were present in the one or more stream(s) that were directed to the methanol/water separation unit 446.

The present invention has been generally discussed herein in terms of eliminating the light ends separation unit and/or the refining column of a methanol synthesis system separation zone. In another embodiment, which operates in a manner substantially identical to the flow schemes discussed above, the methanol/water separation unit of the MTO reaction system is eliminated, and the refining column and/or the light ends separation unit of the methanol synthesis system perform the function of the methanol/water separation of a conventional MTO facility. In this embodiment, the light ends removal unit and/or the refining column may be modified in size, e.g., increased cross-sectional diameter, in order to accommodate the increased volumetric flow of material processed therein.

Having now fully described the invention, it will be appreciated by those skilled in the art that the invention can be performed within a wide range of parameters within what is claimed, without departing from the spirit and scope of the invention.

The invention claimed is:

1. A process for producing light olefins, the process comprising the steps of:
    (a) converting a syngas steam in a methanol synthesis reactor to a first effluent stream containing methanol and water;
    (b) separating the first effluent stream in an integrated methanol/water separation unit comprising a distillation column into a first fraction and a second fraction, wherein the first fraction comprises a majority of the methanol present in the first effluent stream, and wherein the second fraction comprises a majority of the water present in the first effluent stream;
    (c) contacting the methanol in the first fraction with a catalyst in an MTO reactor under conditions effective to form a product effluent containing the light olefins, residual methanol and water;
    (d) separating the product effluent into one or more $C_2$–$C_5$ product streams, and a third fraction, wherein the third fraction contains a majority of the residual methanol and water present in the product effluent; and
    (e) separating in the integrated methanol/water separation unit a majority of the residual methanol present in the third fraction from a majority of the water present in the third fraction, wherein the first fraction further comprises the majority of the residual methanol present in the third fraction, and wherein the second fraction further comprises the majority of the water present in the third fraction, wherein the process further including steps
    (f) providing an initial natural gas stream containing natural gas and one or more compounds containing sulfur;
    (g) removing at least a portion of the one or more compounds containing sulfur from the initial natural gas stream in a desulfurization unit, thereby forming a processed natural gas stream; and
    (h) forming the syngas provided, in step (a) from at least a portion of the natural gas in the processed natural gas stream.

2. The process of claim 1, wherein the process further comprises the step of:
    (i) directing a methane-containing gas and steam to a steam reformer to form the syngas stream of step (a).

3. The process of claim 1, wherein the process further comprises the step of:
    (f) directing a methane-containing gas and oxygen to a partial oxidation reformer to form the syngas stream of step (a).

4. The process of claim 1, wherein step (h) occurs by steam reforming.

5. The process of claim 1, wherein step (h) occurs by partial oxidation.

6. The process of claim 1, wherein step (h) occurs by autothermal reforming.

7. The process of claim 1, wherein step (h) occurs by combined reforming.

8. The process of claim 1, wherein the third fraction comprises less than 10 weight percent light olefins, based on the total weight of the third fraction.

9. The process of claim 1, wherein the third fraction comprises at least 0.5 weight percent methanol, based on the total weight of the third fraction.

10. The process of claim 9, wherein the third fraction comprises at least 5 weight percent methanol, based on the total weight of the third fraction.

11. The process of claim 10, wherein the third fraction comprises at least 20 weight percent methanol, based on the total weight of the third fraction.

12. The process of claim 1, wherein the first fraction comprises less than 20 weight percent water, based on the total weight of the first fraction.

13. The process of claim 12, wherein the first fraction comprises less than 5 weight percent water, based on the total weight of the first fraction.

14. The process of claim 13, wherein the first fraction comprises less than 0.5 weight percent water, based on the total weight of the first fraction.

15. The process of claim 13, wherein the first effluent stream further comprises fusel oil, and wherein the process further comprises the step of:
    (h) removing the fusel oil from the first effluent stream through a side draw stream of the integrated methanol/water separation unit.

* * * * *